United States Patent [19]

Mooberry

[11] Patent Number: 5,196,519

[45] Date of Patent: Mar. 23, 1993

[54] REDUCIBLE COMPOUNDS WHICH PROVIDE ANILINE DYES, AND ANALYTICAL COMPOSITIONS, ELEMENTS AND METHODS USING SAME

[75] Inventor: Jared B. Mooberry, Rochester, N.Y.

[73] Assignee: Eastman Kodak Company, Rochester, N.Y.

[21] Appl. No.: 819,162

[22] Filed: Dec. 4, 1991

Related U.S. Application Data

[62] Division of Ser. No. 215,127, Jul. 5, 1988, Pat. No. 5,108,902.

[51] Int. Cl.$^5$ ............... C07C 245/06; C07C 271/28; G01N 21/78
[52] U.S. Cl. ................... 534/733; 534/596; 534/732; 552/299
[58] Field of Search ............... 534/732, 733; 552/299

[56] References Cited

U.S. PATENT DOCUMENTS

| 4,139,379 | 2/1979 | Chasman et al. | 430/223 X |
| 4,144,306 | 3/1979 | Figueras | 422/56 |
| 4,564,577 | 1/1986 | Begley | 534/732 X |
| 4,610,961 | 9/1986 | Guardino et al. | 435/34 |
| 4,840,884 | 6/1989 | Mooberry et al. | 430/557 |
| 4,857,271 | 8/1989 | Belly et al. | 430/223 X |

Primary Examiner—Mary C. Lee
Assistant Examiner—Fiona Powers
Attorney, Agent, or Firm—J. Lanny Tucker

[57] ABSTRACT

Certain reducible compounds are useful in analytical compositions, elements and methods, for example for the detection of bacterial cells. These compounds comprise a moiety which provides an aniline dye upon reduction. Structurally, the reducible compounds are quinones having suitable substituents which promote varying amounts of aniline dye release at physiological pH.

4 Claims, No Drawings

REDUCIBLE COMPOUNDS WHICH PROVIDE ANILINE DYES, AND ANALYTICAL COMPOSITIONS, ELEMENTS AND METHODS USING SAME

This is a divisional of application Ser. No. 215,127, filed Jul. 5, 1988 now U.S. Pat. No. 5,108,902.

FIELD OF THE INVENTION

This invention relates to clinical chemistry. In particular, it relates to novel reducible compounds and to their use in assays of liquids, such as biological fluids, to release useful dyes. These compounds are especially useful in the detection of microorganisms.

BACKGROUND OF THE INVENTION

Chemical analysis of liquids, such as water, milk and biological fluids is often desirable or necessary for health maintenance and diagnostic care. Various compositions and elements to facilitate such analyses are known. Such compositions and elements generally include a reagent composition for determining a substance under analysis, identified as an "analyte" herein. The analyte can be a living organism or a nonliving chemical substance. The reagent composition, upon interaction with the analyte, provides a detectable change (for example, dye formation).

Recently, much work has been directed to developing compositions and elements which are useful for rapid and highly quantitative diagnostic or clinical analysis of biological fluids such as whole blood, serum, plasma, urine and the like.

For example, for the rapid and effective diagnosis and treatment of infectious diseases, it is desirable to be able to detect the bacteria causing the disease as rapidly as possible. Infections of the urinary tract are among the most common bacterial diseases, second in frequency only to infections of the respiratory tract. In fact, in many hospitals, urinary tract infections are the most common form of nosocomial infections, often following the use of in-dwelling catheters and various surgical procedures. Most urinary tract infections result from ascending infection by microorganisms introduced through the urethra and vary in severity from an unsuspected infection to a condition of severe systemic disease. Such infections are usually associated with bacterial counts of 100,000 ($10^5$) or more organisms per ml of urine, a condition referred to as significant bacteriuria. Under normal conditions, urine is sterile, although contamination from the external genitalia may contribute up to 1,000 ($10^3$) organisms per ml in properly collected and transported specimens.

Significant bacteriuria may be present in a number of pathological conditions involving microbial invasion of any of the tissues of the urinary tract, or may result from simple bacterial multiplication in the urine without tissue invasion. The infection may involve a single site such as the urethra, prostate, bladder, or kidney, although frequently it involves more than one site. Infection restricted to the urine may present itself as asymptomatic bacteriuria, that is, a condition which manifests no overt signs or symptoms of infection. Early treatment of this condition can prevent the development of more serious conditions, for example pyelonephritis (inflammation of the kidney and the renal pelvis). The rapid detection of bacteria by a reliable method would therefore facilitate an early and specific diagnosis.

Further, in order to insure that a prescribed antibiotic is in fact effective in treating an infection, repeated tests during therapy are required. The need for simple, rapid bacteriuria tests is thus clear. Moreover, in view of the frequent unsuspected asymptomatic occurrences of urinary tract infrections among children, pregnant women, diabetics and geriatric populations, diagnosis of which may require collection and testing of several specimens, bacteriuria tests must be sufficiently simple and economical to permit routine performance. Again, this illustrates the need for a rapid and inexpensive bacteriuria detection method.

Current laboratory methods based on culturing microorganisms, for example, the calibrated loop-direct streak method, require significant incubation periods (18-24 hours) before results can be determined. These laboratory methods are also time-consuming to perform and require considerable clinical training and facilities.

Known commercial methods for relatively rapid detection of bacteriuria have serious drawbacks. They are tedious, not completely reliable, require complex reagents or instrumentation, and have limited sensitivity to certain microorganisms and susceptibility to drug or other interferences. Hence, the usefulness of known methods is severely limited.

It is also known that colorless materials, for example, tetrazolium salts, can be reduced by micororganisms to form a colored formazan dye, as described in U.S. Pat. No. 3,415,718 (issued Dec. 10, 1968 to Forkman et al). However, the use of formazan dyes for detecting microorganisms has several drawbacks. The formazan dyes generally have low extinction coefficients and therefore cannot be used to detect low levels of microorganisms. The tetrazolium salts have structures that are not readily modified to increase the extinction coefficients of the formazan dyes. Some formazan dyes are insoluble in water and can be toxic to the microorganisms.

U.S. Pat. No. 4,144,306 (issued Mar. 13, 1979 to Figueras) describes a multilayer element for analysis of liquids. This element can include an interactive composition which interacts with an analyte to release a preformed, detectable moiety from an immobile carrier nucleus upon oxidation or reduction. Such release generally requires the presence of a highly alkaline medium (i.e. pH greater than 13). The spectral absorption band of the preformed detectable moiety is the same before and after release, and radiation-blocking layers are used in the element to screen out unwanted absorption from unreleased detectable moiety during the assay.

copending and commonly assigned U.S. Ser. No. 824,766 (filed Jan. 31, 1986 by Belly et al) describes reducible compounds which when reduced release detectable moieties, such as dyes. These reducible compounds can be used to detect microorganisms or other analytes which will reduce the compounds at physiological pH (generally a pH from 4 to 9). While providing an advance in the art for detecting such materials, the dyes released from the compounds of Belly et al are attached to a quinone or aromatic nucleus through a carbonyl or thiocarbonyl linkage which becomes part of the released dye. This limits the number and variety of dyes which can be incorporated into the Belly et al reducible compounds and used in analytical methods. For example, aniline dyes cannot be released from the Belly et al compounds.

There are many aniline dyes which are potentially useful in analytical methods if only there was a means for releasing them selectively in the presence of an analyte.

SUMMARY OF THE INVENTION

Novel useful reducible compounds which can be reduced to release a wide variety of aniline dyes have the structure CAR—$R^1$ wherein CAR— is the quinone structure

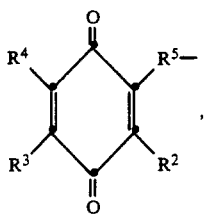

$R^1$ is

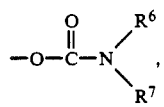

$R^2$ and $R^4$ are independently hydrogen, alkyl, aryl or an electron withdrawing group, $R^5$ is methylene, $R^3$ is the same as —$R^5$—$R^1$, or is hydrogen, alkyl, aryl or an electron withdrawing group, or $R^3$ and $R^4$, taken together, represent the atoms necessary to complete a fused carbocyclic ring, and $R^6$ is alkyl, aryl, cycloalkyl or a heterocyclic group, and $R^7$, together with the nitrogen atom forms an aniline dye, or $R^6$ and $R^7$ taken together form a carbocyclic ring that forms part of an aniline dye moiety which, upon release of $R^1$ from the quinone nucleus and decarboxylation, form an aniline dye.

The reducible compound noted above can be used in a composition which is buffered at a pH of 9 or less with one or more appropriate buffers. Alternatively, the compound can be incorporated in a dry analytical element for the determination of an analyte. This element comprises an absorbent carrier material, and one or more reagent zones in which the reducible compound is located.

A method for the determination of an analyte comprising the steps of:

A. at a pH of 9 or less, contacting a sample of a liquid suspected of containing an analyte with the reducible compound noted above, to provide an aniline dye, and B. detecting the aniline dye provided as a result of the presence of the analyte which effects the release of $R^1$ from the quinone nucleus.

The novel reducible compounds of this invention provide the advantage of providing a means for using a variety of aniline dyes in analytical methods. In comparison to the compounds described in U.S. Ser. No. 824,766 (noted above) wherein the dye moieties are attached through carbonyl or thiocarbonyl linkages, the compounds of this invention have aniline dyes linked to the quinone nucleus through carboxamido linkage.

DETAILED DESCRIPTION OF THE INVENTION

The reducible compounds of this invention are broadly defined as compounds which can be reduced as a result of the presence of an analyte, preferably at a physiological pH (such as from 6 to 9) to release an aniline dye. The presence of the dye can be measured at an appropriate wavelength to determine the amount of analyte in a test specimen.

More particularly, the compounds of this invention are defined by the structure CAR—$R^1$ wherein CAR— is the quinone structure

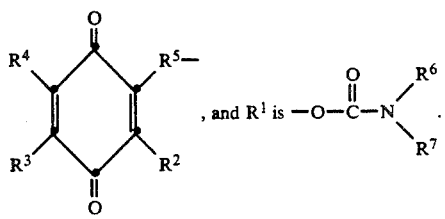

In the quinone nucleus illustrated above, $R^2$ and $R^4$ are independently (that is, the same or different) hydrogen, substituted or unsubstituted alkyl of 1 to 40 carbon atoms (for example methyl, ethyl, hydroxymethyl, methoxymethyl, benzyl and others apparent to one skilled in the art) substituted or unsubstituted aryl (for example phenyl, naphthyl, methylnaphthyl, p-nitrophenyl, m-methoxyphenyl, phenylsulfonamido and others apparent to one skilled in the art) or an electron withdrawing group which generally has a positive Hammett sigma value, and preferably has a sigma value greater than about 0.06. Hammett sigma values are calculated in accordance with standard procedures described, for example in *Steric Effects in Organic Chemistry*, John Wiley & Sons, Inc., 1956, pp. 570–574 and *Progress in Physical Organic Chemistry*, Vol. 2, Interscience Publishers, 1964, pp. 333–339. Representative electron withdrawing groups having positive Hammett sigma values include cyano, carboxy, nitro, halo (fluoro, bromo, chloro or iodo), trihalomethyl (for example trifluoromethyl or trichloromethyl), trialkylammonium, carbonyl, carbamoyl, sulfonyl, sulfamoyl, esters and others readily apparent to one skilled in the art, or alkyl or aryl groups (defined above) substituted with one or more of these electron withdrawing groups. Preferred electron withdrawing groups include p-nitrophenyl, m-nitrophenyl, p-cyanophenyl and 2,5-dichlorophenyl. Aryl groups with methoxy or acetamido groups in the meta position are also useful.

$R^3$ is the same as —$R^5$—$R^1$, or it is hydrogen, substituted or unsubstituted alkyl, substituted or unsubstituted aryl or an electron withdrawing group as defined above for $R^2$ and $R^4$. Alternatively, $R^3$ and $R^4$, taken together, represent the atoms necessary to complete a substituted or unsubstituted fused carbocyclic ring attached to the quinone nucleus. For example, such a ring (mono- or bicyclic) can have from 4 to 8 carbon atoms in the backbone.

$R^5$ is methylene which can be unsubstituted or substituted with methyl or methoxy.

$R^6$ is a substituted or unsubstituted alkyl of 1 to 20 carbon atoms (such as methyl, ethyl, isopropyl, hexyl, —$CH_2CH_2$—OCO-t-butyl and others known in the art), substituted or unsubstituted aryl of 6 to 14 carbon atoms in the nucleus (such as phenyl, naphthyl, p-chlorophenyl and others known in the art), substituted or unsubstituted heterocyclic group of 5 to 10 carbon and hetero (oxygen, sulfur, nitrogen, selenium, tellurium) atoms (such as pyridyl, oxazolyl, thiazolyl and others known in the art) or substituted or unsubstituted cycloalkyl of 5 to 10 carbon atoms (such as cyclopentyl, cyclohexyl and others known in the art).

$R^7$, together with the nitrogen atom to which it is attached, forms an aniline dye moiety which becomes an aniline dye when $R^1$ is released from the quinone nucleus and after decarboxylation. Representative examples of useful aniline dye moieties include, but are not limited to:

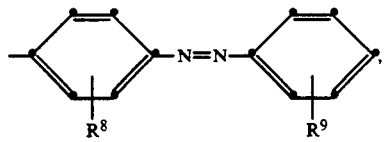

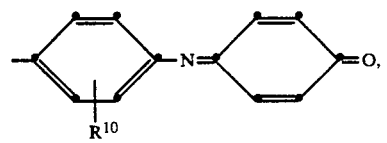

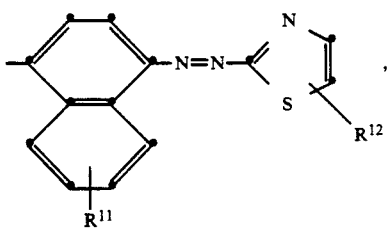

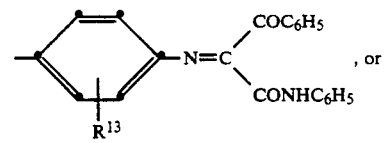

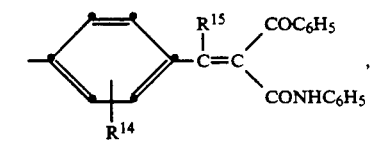

wherein $R^8$, $R^9$, $R^{10}$, $R^{11}$, $R^{12}$, $R^{13}$ and $R^{14}$ are chosen from nitro, sulfoalkyl (of 1 to 3 carbon atoms), tertiary amines (of 1 to 3 carbon atoms), alkoxy (of 1 to 3 carbon atoms), alkyl (of 1 to 3 carbon atoms), halo and others known in the art, and $R^{15}$ is substituted or unsubstituted alkyl (of 1 to 15 carbon atoms) or substituted or unsubstituted aryl (as defined above).

Alternatively, $R^6$ and $R^7$ taken together with the attached nitrogen atom form a 5- to 7-membered carbocyclic ring that is part of the aniline dye moiety. Examples of such moieties include, but are not limited to:

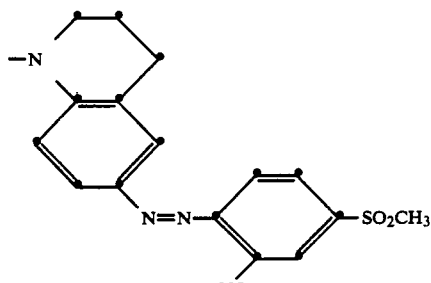

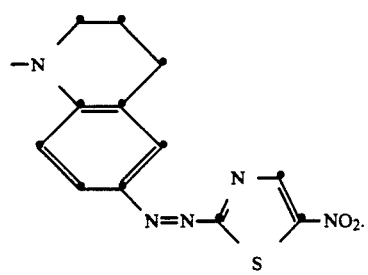

When the reducible compound is reduced, the $R^1$ moiety is released. It contains an unstable carbamic acid linkage which spontaneously undergoes decarboxylation to form an aniline dye. In a preferred embodiment, the released aniline dye has a maximum absorption different than the that of the dye moiety attached to the quinone nucleus. However, in some embodiments, the released aniline dye has the same maximum absorption as that of the attached aniline moiety. Such compounds could be used in analytical elements having a radiation-blocking layer through which the released aniline dye would diffuse into another layer for detection.

The preferred reducible compounds of this invention have at least two electron withdrawing groups for $R^2$, $R^3$ and $R^4$ as defined above, or $R^3$ and $R^4$, taken together represent the atoms necessary to complete a substituted or unsubstituted fused 5- to 7-member carbocyclic ring as defined above. More preferably, $R^5$ is unsubstituted methylene and $R^3$ and $R^4$ are the 5- to 7-membered carbocyclic ring as defined above.

Representative reducible compounds of this invention include, but are not limited to:

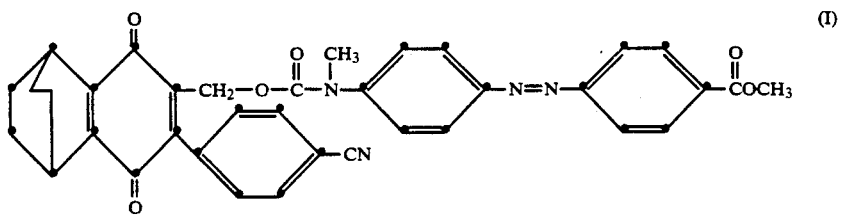

(I)

-continued
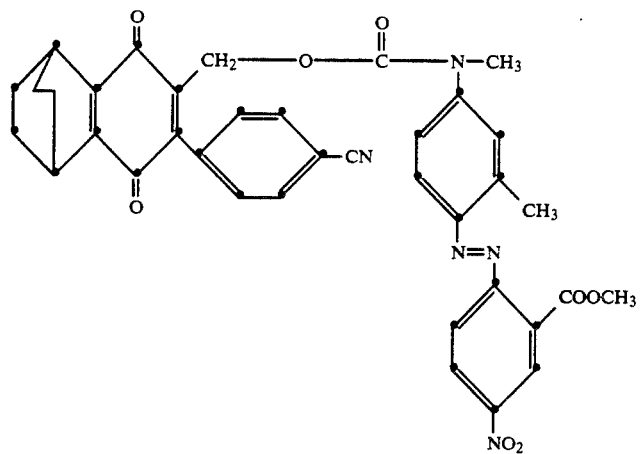
(II)
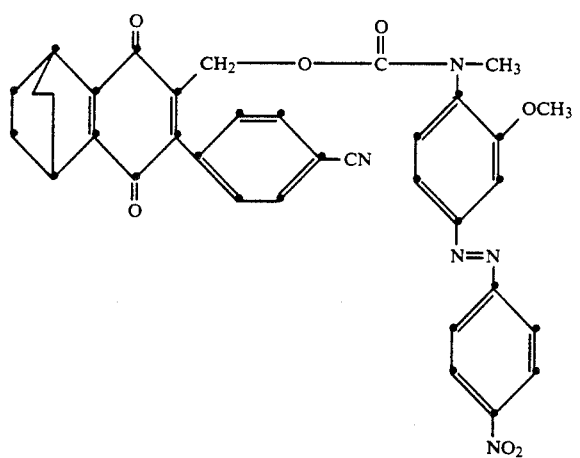
(III)
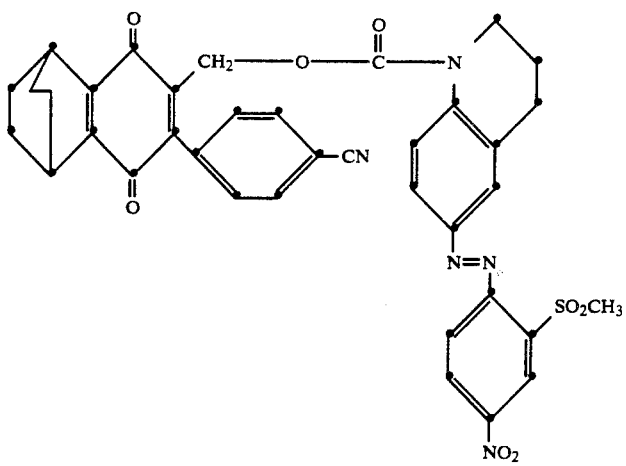
(IV)

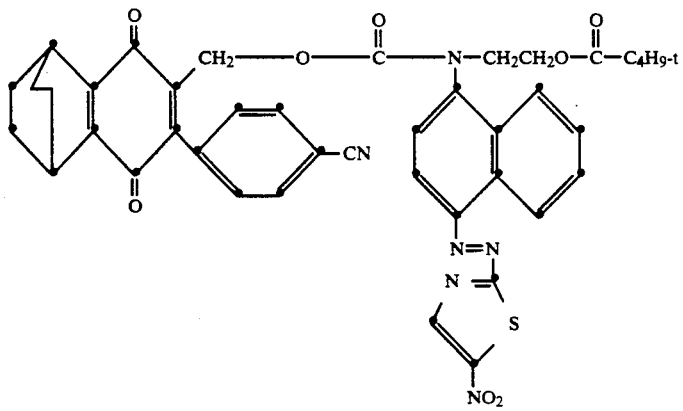

(V)

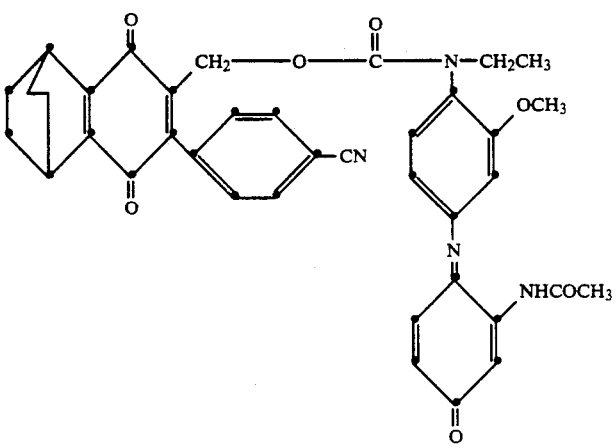

(VI)

Compound I is preferred.

The novel reducible compounds of the present invention are prepared using a sequence of individually known reactions. Generally, the preparation sequence includes the following general steps: (1) preparation of the aniline dye, (2) preparation of the aniline dye carbamyl chloride, and (3) reaction of the carbamyl chloride and a hydroxymethyl CAR— nucleus. Representative preparations are provided in Examples 1 and 2 below.

Generally, the reducible compounds described herein have limited water solubility. Hence, it is best, when using them in an aqueous environment, to prepare a dispersion of the compound prior to use. Such dispersions generally comprise the reducible compound, an aqueous buffer solution and either a water-solubilizing surfactant or a water-miscible organic solvent for the compound, or both.

Surfactants which are useful in the practice of this invention include any surfactants which do not inhibit compound reduction. Generally, for detection of living cells, the useful surfactants are nonionic surfactants, including, for example, alkylarylpolyethoxy alcohols (for example, TRITON X-100 and X-305 available from Rohm & Haas), p-alkylaryloxypolyglycidols (for example, SURFACTANT 10G available from Olin Corp.), TWEEN 80 (available from ICI Americas, Inc.), and others known to one skilled in the art.

Useful water-miscible organic solvents include, but are not limited to, alcohols (for example, methanol, ethanol, propanol and others known in the art), N,N-dimethylformamide, dimethyl sulfoxide, acetonitrile or hexamethylenephosphoramide. The particular solvent to be used for a particular reducible compound can be readily determined by routine experimentation.

A dispersion can be prepared in the following general manner with the particular details of such a preparation illustrated in Example 3 below. The reducible compound is dissolved in the water-miscible solvent at a concentration which depends upon its molecular weight, but generally at from about 1 to about 100, and preferably from about 5 to about 80, mg per ml of solvent. The resulting solution is then mixed with a suitable surfactant in an amount generally of from about 0.1 to about 24, and preferably from about 0.5 to about 10, mg surfactant per ml of dispersion. This preparation is generally carried out at room temperature.

These dispersions generally contain a buffer in an amount effective to maintain physiological pH (generally 4 to 9). The concentration of buffer in the dispersion can vary widely, but is generally from about 0.01 to about 0.1 molar. Representative buffers include phosphates, borates and others reported by Good et al in Biochemistry, 5, 467 (1966), and Anal. Biochem., 104, 300 (1980).

The reducible compounds described herein are useful in compositions for analytical determination (that is, qualitative or quantitative detection) of aqueous and nonaqueous liquids, for example, biological fluids, manufacturing processes, wastewater or food stuffs. Determinations can be made of various analytes using a single reaction or a sequence of reactions which bring about reduction of the compound and release of the aniline dye. The various analytes include living cells (for example, bacteria, white blood cells, yeast or fungi), enzymes (for example, lipase, glucose oxidase, lactate oxidase, creatine kinase, α-glycerophosphate oxidase, lactate dehydrogenase, pyruvate dehydrogenase, glucose-6-phosphate dehydrogenase, alanine aminotransferase, aspartate aminotransferase and other NADH-based, FADH-based or oxidase-based assays), biological or chemical reductants other than living cells which will reduce the reducible compound (for example, ascorbates, cysteine, glutathione or thioredoxin), metabolizable substances (for example, glucose, lactic acid, triglycerides or cholesterol) and immunoreactants (for example, antigens, antibodies or haptens).

The compositions can be used to monitor enzyme redox reactions as well as flavin adenine dinucleotide (FAD-FADH)-based and nicotinamide adenine dinucleotide (NAD-NADH)-based and (NADP-NADPH)-based reactions. In such instances, the reducible compound can be used to provide a dye in place of NADH.

The reducible compounds of this invention, are particularly useful in detecting or quantifying living cells in biological samples. Although any biological sample suspected of having living cells therein can be analyzed for bacteria, white blood cells, yeast or fungi by this invention, the invention is particularly useful for bacterial detection in biologial fluids, such as human and animal fluids (for example, urine, cerebral spinal fluid, blood as well as stool secretions) and suspensions of human or animal tissue. The practice of this invention is particularly important for detection of urinary tract infections in urine (diluted or undiluted).

When determining living cells using the reducible compounds, it is preferable that the living cells interact with an electron transfer agent (herein ETA). The presence of an ETA may also provide more efficient dye release for analytical determinations of nonliving analytes. The ETA is a mobile compound which acts as an intermediary between the substance being determined (for example, living cell) and the reducible compound.

In general, the potential of the ETA should be more positive than the potential of the substance to be determined and less positive than the potential of the reducible compound of this invention. That is, the ETA should be more easily reduced than the analyte and less easily reduced than the reducible compound. They are generally present at a concentration that is dependant upon the concentration of the analyte, and preferably at a concentration of from about $1 \times 10^{-3}$ molar to about $1 \times 10^{-7}$ molar.

ETA compounds useful in the practice of this invention include phenazine methosulfate, phenazine ethosulfate and similar compounds known to one skilled in the art. Combinations of different ETA compounds can be used if desired. Preferred ETA compounds useful in the practice of this invention are the subject of U.S. Ser. No. 699,374 of Mura et al, filed Feb. 7, 1985. In general, those compounds are substituted benzo- and naphthoquinones.

The detection of living cells, and particularly of bacterial cells, is often carried out in the presence of a nutrient for those cells although its presence is not essential. Any nutrient media can be used which contains useful carbon, and optionally nitrogen, sources. Suitable nutrient media having proper components and pH are well known in the art. Particularly useful nutrients are glucose or tryptose alone or in combination.

The present invention is adaptable to either solution or dry assays. In a solution assay, a solution (or dispersion) containing a reducible compound, and preferably an ETA, is prepared and contacted with a liquid test sample containing the living cells or analyte to be determined by mixing. The ETA can also be mixed with the test sample prior to mixing with the reducible compound. Generally the reducible compound is mixed with the test sample in a suitable container (for example, test tube, petrie dish beaker or cuvette). The resulting solution (or dispersion) is gently mixed and incubated for a relatively short time at a temperature up to about 40° C. The test sample is then evaluated by measuring the dye at a suitable wavelength. Such an evaluation can be done with suitable detection equipment.

A solution assay can also be carried out by contacting a porous, absorbent material, for example a paper strip, containing the test sample with a dispersion of the reducible compound. The analyte in the test sample can migrate from the porous material into the dispersion and initiate the analytical reactions needed for determination. In solution assays, the amount of reducible compound present is at least about 0.001, and preferably from about 0.01 to about 1.0, millimolar. Other reagents can be present in amounts readily determined by one skilled in the art.

Alternatively, the method of this invention can be practiced in a dry assay with a dry analytical element. Such an element can be a absorbent carrier material, that is, a thin sheet or strip of self-supporting absorbent or bibulous material, such as filter paper or strips, which contains the reducible compound or a dried residue of the dispersion comprising same. Such elements are known in the art as test strips, diagnostic elements, dip sticks, diagnostic agents and the like.

When employed in dry analytical elements, the reducible compounds described herein can be incorporated into a suitable absorbent carrier material by imbibition or impregnation, or can be coated on a suitable absorbent carrier material. Alternatively, they can be added to the element during an assay. Useful carrier materials are insoluble and maintain their structural integrity when exposed to water or biological fluids such as urine or serum. Useful carrier materials can be prepared from paper, porous particulate structures, cellulose, porous polymeric films, wood, glass fiber, woven and nonwoven fabrics (synthetic and nonsynthetic) and the like. Useful materials and procedures for making such elements are well known in the art as exemplified by U.S. Pat. Nos. 3,092,465 (issued Jun. 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 to Kitajima et al), and 4,270,920 (issued Jun. 2, 1981 to Kondo et al), and U.K. Patent 2,052,057 (published Jan. 21, 1981).

A dry assay can be practiced to particular advantage with an analytical element comprising a nonporous support having thereon at least one porous spreading zone as the absorbent carrier material. The reducible compound can be in the spreading zone or in a different zone (for example, reagent zone, registration zone or hydrophilic zone). The spreading zone can be prepared from any suitable fibrous or non-fibrous material or mixtures of either or both. The void volume and average pore size of this zone can be varied depending upon the use intended. For example, if whole blood or other liquid samples containing cells or high molecular weight materials are to be assayed, the void volume and average pore size are generally greater than if serum or urine is to be assayed.

The spreading zone can be prepared using fibrous materials, either mixed with a suitable binder material or woven into a fabric, as described in U.S. Pat. No. 4,292,272 (issued Sep. 29, 1981 to Kitajima et al), from polymeric compositions (for example, blush polymers) or particulate materials, with or without binding adhesives, as described in U.S. Pat. Nos. 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese Patent Publication 57(1982)-101760 (published Jun. 24, 1982). It is desired that the spreading zones be isotropically porous, meaning that the porosity is the same in each direction in the zone as created by interconnected spaces or pores between particles, fibers or polymeric strands.

The dry analytical element of this invention can be a single self-supporting porous spreading zone containing a reducible compound and any other desired reagents for a particular use, but preferably such zone is carried on a suitable nonporous support. Such a support can be any suitable dimensionally stable, and preferably, transparent (that is, radiation transmissive) film or sheet material which transmits electromagnetic radiation of a wavelength between about 200 and about 900 nm. Useful support materials include polystyrene, polyesters, polycarbonates and cellulose esters.

The elements can have more than one zone which are generally in fluid contact with each other, meaning that fluids, reagents and reaction products can pass between superposed regions of adjacent zones. Preferably, the zones are separately coated superposed layers, although two or more zones can be in a single coated layer. Besides the patents noted above, suitable element formats and components are described also, for example, in U.S. Pat. Nos. 4,042,335 (issued Aug. 16, 1977 to Clément) and 4,144,306 (noted above) and Re. 30,267 (reissued May 6, 1980 to Bruschi).

In the elements of this invention, the amount of the reducible compound can be varied widely, but it is generally present in a coverage of at least about 0.01, and preferably from about 0.05 to about 0.2, g/m$^2$. Optional, but preferred reagents are generally present in the following coverages:

ETA: generally at least about 0.001, and preferably from about 0.01 to about 1, g/m$^2$, nutrient: generally at least about 0.05, and preferably from about 0.1 to about 2, g/m$^2$ (used only in living cell detection), buffer (pH$\leq$9): generally at least about 0.1, and preferably from about 0.5 to about 2, g/m$^2$, and surfactant: generally at least about 0.1, and preferably from about 0.2 to about 5, g/m$^2$.

One or more of the zones can contain a variety of other desirable, but optional, components, including activators, binders (generally hydrophilic), antioxidants or coupler solvents as is known in the art, as well as any reagents needed for assay of a particular analyte.

In one embodiment of this invention, an element for detection of microorganisms in an aqueous liquid comprises an electron transfer agent and a reducible compound, both of which are described above. It is desirable that these elements also contain a nutrient for the living cells and a buffer which maintains physiological pH during the assay. Such an element can be used to detect bacteria, for example, in a urine sample (for example, one pretreated to eliminate reductive interferents) by physically contacting the sample and element in a suitable manner, and detecting the detectable species released from the reducible compound as a result of the presence of the bacteria at the appropriate wavelength.

In another embodiment of this invention, an element is used for the determination of a nonliving biological or chemical analyte in an aqueous liquid. An interactive composition containing one or more reagents can be incorporated into the element or added at the time of the assay. This composition contains the reagents needed to interact with the analyte to bring about reduction of the reducible compound and eventual dye formation. Examples of such analytes are described above. The amount of dye detected can be correlated to the amount of analyte present in the liquid sample.

The element of this invention is also useful for determining other reductants such as ascorbate (ascorbic acid and equivalent alkali metal salts), cysteine, glutathione, thioredoxin and the like.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, an analyte or living cell determination is made by taking the element from a supply roll, chip packet or other source and contacting it with a sample (for example, 1–200 $\mu$l) of the liquid to be tested so that the sample mixes with the reagents in the element. Such contact can be accomplished in any suitable manner, for example, by dipping or immersing the element into the sample or, preferably, by spotting the element by hand or machine with one or more drops of the sample with a suitable dispensing means.

After sample application, the element is exposed to any conditioning, such as incubation, heating or the like, that may be desirable to quicken or otherwise facilitate obtaining any test result.

Detection of an analyte or living cell is achieved when the reducible compound is reduced releasing an aniline dye which can be detected in a suitable manner. Spectral determinations can be made either at the maximum wavelength of the dye or at wavelengths other than the maximum wavelength.

Reagents used in the following representative examples were obtained as follows: ascorbic acid, sodium salt, nicotinamide adenine dinucleotide, reduced form (NADH) and phenazine methosulfate from Sigma Chemical Co., brain heart infusion (BHI) media from Difco Labs, TRITON X-100 surfactant from Rohm & Haas, titanium (IV) chloride and sodium borohydride (10% on alumina) from Morton-Thiokol, Inc., Alfa Products, and the bacterial microorganisms from the American Type Culture Collection (ATCC) in Rockville, Md. All other reagents were either obtained from Eastman Kodak or prepared using known starting materials and procedures.

The following examples are presented to illustrate the practice of this invention.

EXAMPLE 1

Preparation of Reducible Compound I

Reducible Compound I identified above was prepared as follows:

Preparation of Carbamyl Chloride Intermediate:

Azoaniline dyes can be prepared by published methods (see for example, diazonium coupling in March, *Advanced Organic Chemistry*, 3rd Ed., John Wiley & Sons, p. 471, 1985).

The azoaniline dye (540 mg, 2 mmole) was dissolved in dichloromethane (50 ml) containing 2,6-lutidine (214 mg). A solution of phosgene (2 ml of a 1 molar solution in toluene) was added with stirring. The reaction was completed in about 5 minutes as shown by the formation of a new product on thin layer chlromatography (silica; heptane/diethylether, 1:1). The reaction mixture was then poured into dilute aqueous hydrochloric acid (100 ml), the organic layer was separated, dried and concentrated to yield a solid product. The carbamyl chloride was purified by slurrying in diethylether/ethyl acetate solution and used directly in the next step.

Preparation of Hydroxymethyl Quinone Intermediate:

The following reaction sequence was followed to prepare this intermediate.

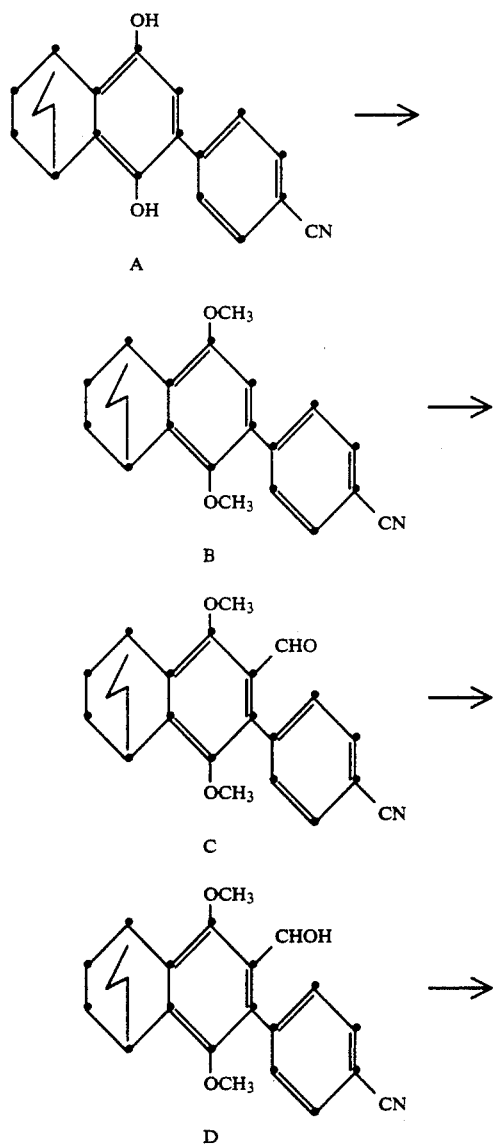

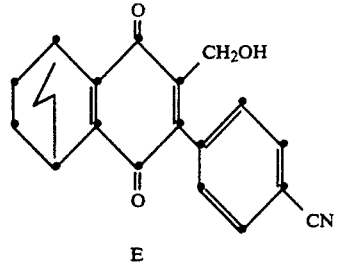

E

Compound A (identified above) was prepared by the procedure described in copending and commonly assigned U.S. Ser. No. 824,766 (filed Jan. 31, 1986 by Belly et al), Example 21 and Example 1 (Steps 2a, 2b and 3).

Compound A (25.2 g, 86.4 mmole), iodomethane (49 g, 346 mmole) and potassium carbonate (35.8 g, 259 mmole) were heated at reflux in acetone (150 ml) for 24 hours. The reaction mixture was allowed to cool and then poured into dilute hydrochloric acid in ice/water (200 ml). The precipitated solid was collected by filtration and washed with water, air dried and recrystallized from ethanol with decolorizing carbon to give 16.75 g (60.6% yield) of Compound B (m.p. 186°–187° C.). The structure (identified above) was confirmed by NMR.

Titanium (IV) chloride (38 g, 0.2 mole) was added to an ice cold solution of Compound B (32 g, 0.1 mole) in dichloromethane (750 ml), stirring under a nitrogen atmosphere. To this solution was added dropwise α,α-dichloromethylmethylether (18.9 g, 0.165 mole), and the reaction mixture was allowed to warm to room temperature over about 15 hours. The mixture was again cooled and ice water (1 liter) was carefully added dropwise. The resulting layers were separated and the water layer was washed with dichloromethane. The combined organic layers were dried and the solvent was removed. The crude product was purified by chromatography (silica; dichloromethane) and the resulting solid was triturated in cold diethylether, filtered and washed with cold diethylether to give Compound C (16.1 g, 46.5% yield) as a while solid (m.p. 208°–210° C.). The structure (identified above) was confirmed by NMR.

Sodium borohydride (10% on alumina, 27.9 g, 73.5 mmole) was added to a suspension of Compound C (15 g, 43.2 mmole) in ethyl acetate (400 ml). After stirring for one hour at room temperature, the reaction mixture was filtered and the alumina was washed with ethylacetate. The filtrate was freed of solvent to give 16 g of crude Compound D. The structure (identified above) was confirmed by NMR.

Ceric ammonium nitrate (75.3 g, 137 mmole) in water (150 ml) was rapidly added dropwise to a suspension of Compound D (16 g, 45.8 mmole) in acetonitrile (265 ml) and water (15 ml). After stirring two hours at room temperature, the reaction mixture was poured into ice/water (500 ml) and the precipitated product was collected, washed with water and air dried. The crude product was purified by chromatography (silica; dichloromethane/diethylether), and filtered to give 9.4 g (64% yield) of Compound E (m.p. 219°–221° C.). The structure (identified above) was confirmed by NMR.

Preparation of Reducible Compound I:

The hydroxymethylquinone (319 mg, 1 mmole) and the carbamyl chloride (332 mg, 1 mmole) were dissolved in dry dichloromethane (5 ml) at 0° C. With stirring, 4-N,N-dimethylaminopyridine (122 mg, 1 mmmole) and 1,8-diazabicyclounden-7-ene (152 mg, 1 mmole) were then added. After 10 minutes, the reaction mixture was poured into dilute aqueous hydrochloric acid (10 ml) and the organic layer was separated. Thin layer chromatography (silica; dichloromethane/1% trifluoroacetic acid) showed a new compound plus starting materials. Preparative silica thin layer chromatography plates were used to purify the compound. The plates were dipped into a solution of hydrochloric acid/methanol/diethylether (1:1:10), dried and spotted with a dichloromethane solution of the crude product. The plates were developed over 48 hours using dichloromethane and 1% diethylether. The product separated on the plates as a yellow band. The bands were scraped off the plates, dissolved in dichloromethane and filtered through silica (treated with 1% trifluoroacetic acid) using dichloromethane and 1% diethylether as solvents. The solvent was removed and the product was crystallized from diethylether (yield 120 mg). The structure was confirmed by NMR.

EXAMPLE 2

Preparation of Reducible Compound II

The hydroxymethylquinone, aniline dye and carbamyl chloride intermediates were prepared by the procedure described in Example 1.

The reaction between the hydroxymethylquinone and the aniline dye carbamyl chloride was also carried out as described in Example 1. The reaction was completed in about one hour as determined by thin layer chromatography (silica; treated with 1% trifluoroacetic acid), and eluting with dichloromethane with 1% diethylether and heptane/ethyl acetate (3:1). Preparative thin layer chromatography was used to purify the crude product, developing with dichloromethane and 1% diethylether. Reducible Compound II separated as a yellow band, and was obtained as a oil. The structure was confirmed by NMR.

EXAMPLE 3

Detection of E. coli Using Compound I

This example demonstrates the practice of this invention to determine a microorganism, E. coli, in a solution assay using one of the reducible compounds of this invention.

Materials:

E. coli cells were grown in brain heart infusion broth without shaking at 37° C. overnight. Forty ml of cells were harvested by centrifugation, and the pellet was resuspended in 25 ml of 0.05 molar potassium phosphate buffer (pH 7.5), and the resulting suspension was centrifuged. The second pellet was washed and resuspended in 25 ml buffer. An aliquot of this suspension was diluted with buffer to obtain a stock solution of $5 \times 10^8$ E. coli cells/ml ($OD_{620}=0.833$).

A dispersion of Reducible Compound I was prepared as follows: the compound (8 mg) was dissolved in N,N-dimethylformamide (500 μl) which had been acidified with 0.1% concentrated sulfuric acid. A sample (250 μl) of this solution was added to TRITON X-100 nonionic surfactant (500 μl), mixed well and added to 25 ml of 0.05 normal potassium phosphate buffer (pH 7.5).

Trimethylbenzoquinone was used as the electron transfer agent (ETA), with a 0.01 molar solution (1.5 mg/ml) was prepared in methanol.

Glucose was dissolved is distilled water to obtain a 10% (V/V) solution.

Assay:

A test solution was prepared from 1.39 ml of buffer, $1 \times 10^7$ E. coli/ml buffer, 25 μl glucose solution, 1.5 ml of Reducible Compound I suspension and 25 μl of ETA solution.

A Control solution for background contained the same reagents except cells and the buffer volume was 1.45 ml.

Test and Control solutions were incubated at 37° C. for 30 minutes and the optical density was measured at 438 nm. After 30 minutes, the background corrected optical density was 0.477, indicating that Reducible Compound I was useful for detecting the microorganisms.

The invention has been described in detail with particular reference to preferred embodiments thereof, but it will be understood that variations and modifications can be effected within the spirit and scope of the invention.

I claim:

1. A reducible compound of the structure CAR—$R^1$ wherein CAR— is the quinone structure

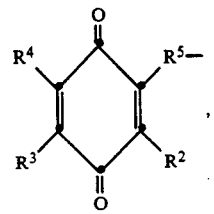

$R^1$ is

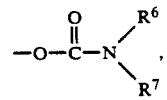

$R^2$ and $R^4$ are independently hydrogen, alkyl, aryl or an electron withdrawing group, $R^5$ is methylene, $R^3$ is the same as —$R^5$—$R^1$, or is hydrogen, alkyl, aryl or an electron withdrawing group, or $R^3$ and $R^4$, taken together, represent the atoms necessary to complete a fused carbocyclic ring, $R^6$ is alkyl, aryl, cycloalkyl or a heterocyclic moiety, and $R^7$, together with the nitrogen atom forms an aniline dye, or $R^6$ and $R^7$ taken together form a ring that forms part of an aniline dye moiety which, upon release of $R^1$ from said quinone nucleus and decarboxylation, form an aniline dye.

2. The compound of claim 1 wherein at least two of $R^2$, $R^3$ and $R^4$ are independently electron withdrawing groups, or $R^3$ and $R^4$, taken together, represent the atoms necessary to complete a fused 5- to 7-member ring.

3. The compound of claim 2 wherein $R^3$ and $R^4$, taken together, represent the atoms necessary to complete a fused 5- to 7-membered ring, and $R^5$ is methylene.

4. The compound of claim 1 selected from the following group of compounds:

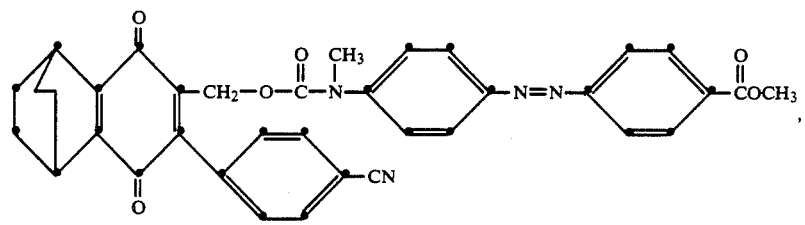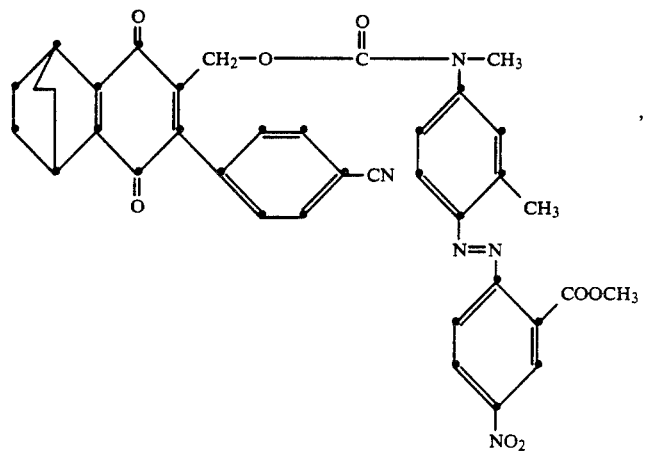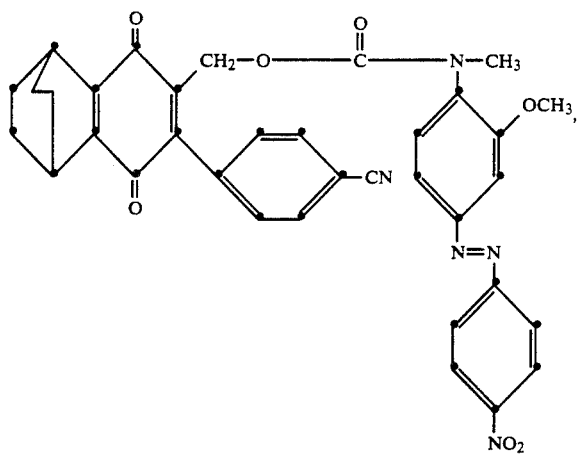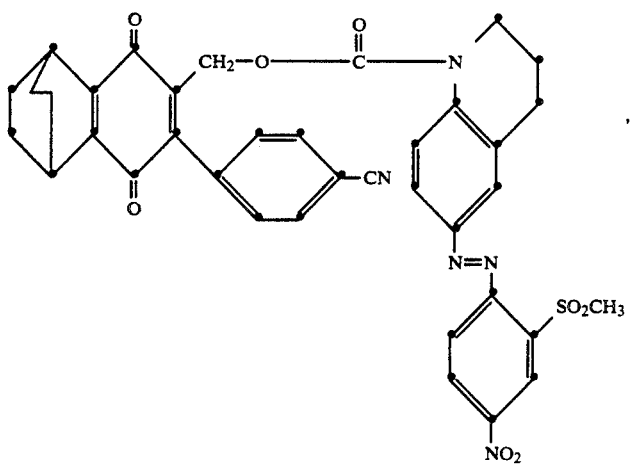

-continued
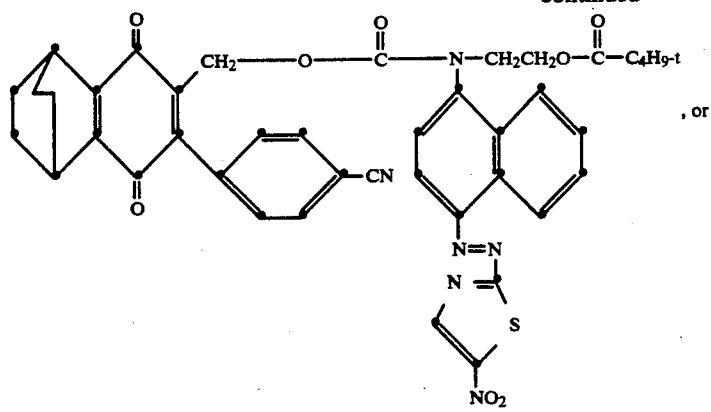
, or
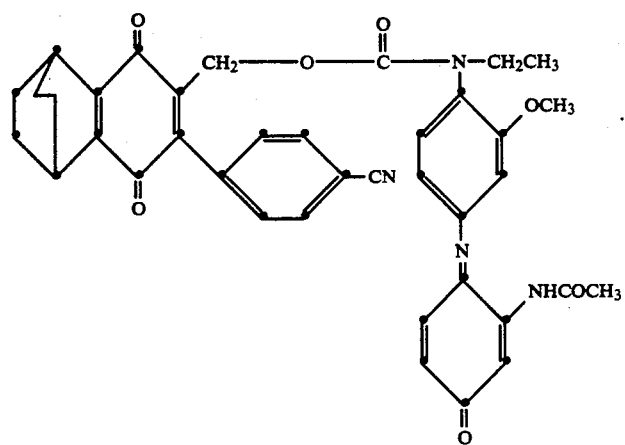
* * * * *